United States Patent [19]
Di Milia et al.

[11] Patent Number: 5,369,033
[45] Date of Patent: Nov. 29, 1994

[54] SUPERCRITICAL FLUID CONTAMINATION MONITOR

[75] Inventors: Edward S. Di Milia, Gardena; Darrell A. Gleichauf, Redondo Beach; Thomas E. Whiting, Hermosa Beach, all of Calif.

[73] Assignee: Hughes Aircraft Company, Los Angeles, Calif.

[21] Appl. No.: 828,533

[22] Filed: Jan. 24, 1992

[51] Int. Cl.$^5$ .................................. G01N 15/00
[52] U.S. Cl. ........................... 436/148; 73/24.03; 73/24.06; 73/863.22; 73/863.24; 422/73; 422/83
[58] Field of Search ............. 422/70, 89, 73, 83; 436/43, 148; 73/863, 863.03, 863.21, 863.22, 863.24, 24.03, 24.06

[56] References Cited

U.S. PATENT DOCUMENTS

| | | | |
|---|---|---|---|
| 3,863,495 | 2/1975 | Schulz et al. | 73/61.1 C |
| 4,124,528 | 11/1978 | Modell | 252/411 |
| 4,434,028 | 2/1984 | Eppig et al. | 196/14.52 |
| 4,597,943 | 7/1986 | Sugiyama et al. | 422/70 |
| 4,735,081 | 4/1988 | Luoma et al. | 73/24.06 |
| 4,872,316 | 10/1989 | Browne et al. | 73/863.21 |
| 4,917,499 | 4/1990 | Champetier et al. | 374/14 |
| 5,009,746 | 4/1991 | Hossain et al. | 162/5 |
| 5,056,355 | 10/1991 | Hepher et al. | 73/24.03 |

FOREIGN PATENT DOCUMENTS 0444946 9/1991 European Pat. Off.

OTHER PUBLICATIONS

J. P. Friedrich et al "Petroleum-free extraction of oil from soybeans with supercritical $CO_2$," *Journal of the American Oil Chemists Society*, vol. 59, No. 7, Jul. 1982, pp. 288-292.

R. Vollbrecht, "Extraction of hops with supercritical $CO_2$", *Chemistry and Industry*, No. 12, Jun. 1982, pp. 397-399.

Grimmett, "The use of liquid carbon dioxide for extracting material products," *Chemistry and Industry*, May 1981, pp. 359-362.

W. W. Schulz and W. H. King, "A Universal Mass Detector for Liquid Chromatography", *Journal of Chromatographic Science*, vol. 11 (Jul. 1973), pp. 343-348.

A. W. Warner "Micro Weighing with the Quartz Crystal Oscillator—Theory and Design", pp. 137-161, in Wolsky and Zdanuk, ed. Ultra Micro Weight Determination in Controlled Environments, Interscience Publishers, 1969.

*Primary Examiner*—Jill A. Johnston
*Attorney, Agent, or Firm*—M. E. Lachman; M. W. Sales; W. K. Denson-Low

[57] ABSTRACT

A system for monitoring changes in the amount of contaminants present in a flowing stream of supercritical fluid. A sample stream is removed from a flowing stream of supercritical fluid and subjected to reduced pressure. The supercritical fluid turns into gas at the reduced pressure with the contaminants remaining in a non-gaseous form. A quartz crystal microbalance system measures changes in the amount of non-gaseous contaminants present in the sample stream. The system is useful in monitoring both cleaning processes and extraction processes utilizing supercritical fluids.

20 Claims, 2 Drawing Sheets

SUPERCRITICAL FLUID CONTAMINATION MONITOR

BACKGROUND OF THE INVENTION

1. Field of the Invention

The present invention relates generally to the use of dense fluids for cleaning materials. More particularly, the present invention relates to monitoring changes in the amount of contaminants present in the dense fluids as the cleaning process progresses.

2. Description of Related Art

Conventional solvent-aided cleaning processes are currently under severe scrutiny due to problems with air pollution and ozone depletion. In addition, recent environmental concerns mandate that many of the organic solvents used in these processes be banned or their use severely limited. The use of dense phase gases for cleaning a wide variety of materials has been under investigation as an alternative to the above-mentioned solvent based cleaning processes. A dense phase gas is a gas compressed under either supercritical or subcritical conditions to liquid-like densities. These dense gases are referred to as dense fluids. Unlike organic solvents, such as n-hexane, or 1,1,1-trichloromethane, dense phase gas solvents exhibit unique physical properties such as low surface tension, low viscosity, high diffusivity and variable solute carrying capacity.

The solvent properties of compressed gases are well known. In the late 1800's, Hannay and Hogarth found that inorganic salts could be dissolved in supercritical ethanol and ether (J. B. Hannay and H. Hogarth, *J. Proc. Rov. Soc.* (London, 29, p. 324, 1897). By the early 1900's, Buchner discovered that the solubility of organics such as naphthalene and phenols in supercritical carbon dioxide increased with pressure (E. A. Buchner, *Z. Physik. Chem.*, 54, p. 665, 1906). Within forty years Francis had established a large solubility database for liquified carbon dioxide which showed that many organic compounds were completely miscible (A. W. Francis, *J. Phys. Chem.*, 58, p. 1099, 1954).

In the 1960's there was much research and use of dense gases in the area of chromatography. Supercritical fluids (SCF) were used as the mobile phase in separating non-volatile chemicals (S. R. Springston and M. Novotny, "Kinetic Optimization of Capillary Supercritical Chromatography using Carbon Dioxide as the Mobile Phase", *CHROMATOGRAPHIA*, Vol. 14, No. 12, p. 679, December 1981). Today the environmental risks and costs associated with conventional solvent-aided separation processes require industry to develop safer and more cost-effective alternatives.

The volume of current literature on solvent-aided separation processes using dense carbon dioxide as a solvent is evidence of the extent of industrial research and development in the field. Documented industrial applications utilizing dense fluid cleaning include extraction of oil from soybeans (J. P. Friedrich and G. R. List and A. J. Heakin, "Petroleum-Free Extracts of Oil from Soybeans", *JAOCS*, Vol. 59, No. 7, July 1982), decaffination of coffee (C. Grimmett, *Chem. Ind.*, Vol. 6, p. 228, 1981), extraction of pyridines from coal (T. G. Squires, et al., "Supercritical Solvents. Carbon Dioxide Extraction of Retained Pyridine from Pyridine Extracts of Coal", *FUEL*, Vol. 61, November 1982), extraction of flavorants from hops (R. Vollbrecht, "Extraction of Hops with Supercritical Carbon Dioxide", *Chemistry and Industry, Jun.* 19, 1982), and regenerating absorbents (activated carbon) (M. Modell, "Process for Regenerating Adsorbents with Supercritical Fluids", U.S. Pat. No. 4,124,528, issued Nov. 7, 1978).

Electro-optical devices, lasers and spacecraft assemblies are fabricated from many different types of materials having various internal/external geometrical structures which are generally contaminated with more than one type of contamination. These highly complex and delicate systems are generally classified together as "complex hardware". Conventional cleaning techniques for removing contamination from such complex hardware requires that the hardware be continually cleaned during assembly. The use of supercritical fluids, such as carbon dioxide is particularly well-suited for cleaning such complex hardware.

Supercritical fluid cleaning systems operate at high temperatures and pressures. As a result, real time monitoring of the cleaning process is difficult. In current systems, parts and materials are cleaned or extracted for a period of time and then removed and tested for cleanliness. If the part is still contaminated, it must be reintroduced into the system and recleaned. In order to avoid having to reclean numerous parts, the parts are typically left in the system much longer than necessary to insure adequate cleanliness. This, of course, results in a great deal of unnecessary cleaning, waste of time, and increased costs.

Experimental supercritical cleaning has used U-V fluorescence detection for in-situ monitoring as described, for example, by Keith M. Motyl, in "Cleaning Metal Substrates Using Liquid/Supercritical Fluid $CO_2$." *NASA Tech Briefs*, December 1990. However, this technique provides a sensitivity on the order of parts per million (ppm) which is not sufficient for precision cleaning requirements. Sensitivity on the order of parts per billion (ppb) is required for precision cleaning.

It would be desirable to provide a system for monitoring supercritical fluid cleaning systems to determine when the particular part has been completely cleaned or when the extraction of desired materials has been completed. Such a monitoring system should be simple, efficient and capable of being used in monitoring a wide variety of cleaning/extraction processes utilizing supercritical fluids. This system should also have a sensitivity on the order of parts per billion in order to be useful for precision cleaning.

SUMMARY OF THE INVENTION

In accordance with the present invention, it was discovered that quartz crystal microbalances may be utilized as part of a system to provide accurate monitoring of supercritical fluid cleaning processes. Quartz crystal microbalances when used in accordance with the present invention, are useful in monitoring the supercritical fluid cleaning/extraction of a wide variety of materials.

The present invention is based upon a system for monitoring changes in the amount of contaminants present in a flowing stream of supercritical fluid. During supercritical fluid cleaning and/or extraction processes, the amount of material, i.e. contaminants, in the flowing stream of supercritical fluid gradually decreases as the process continues. As the amount of contaminants decreases, the change in the amount of contaminants also decreases. Accordingly, monitoring of the change in the amount of contaminants present in the flowing stream of supercritical fluid provides an accurate and reliable real-time indication of the degree of cleanliness or extraction.

As a feature of the present invention, a sample stream of supercritical fluid is removed from the main cleaning or extraction stream. The sample stream of supercritical fluid is introduced into a low pressure measurement zone where the fluid is converted into a gas and the contaminants remain in a non-gaseous form. A quartz crystal microbalance system is provided for measuring changes in the amount of non-gaseous contaminants which are introduced into the measurement zone. As the cleaning and/or extraction procedure approaches completion, the change in amount of contaminants introduced into the measurement zone will also approach zero. The extreme sensitivity of quartz crystal microbalance systems to changes in mass makes the system especially well-suited for determining completion of the cleaning/extraction process.

As another feature of the present invention, a valve is provided to allow selective introduction of the sample stream into the measurement zone. During the early stages of the cleaning process, contaminant levels in the supercritical fluid are generally high. The valve is kept closed during this initial period to prevent the introduction of large amounts of contaminants into the measurement zone which will quickly foul the quartz crystal microbalance. The valve remains closed until sufficient processing time has elapsed and contaminant levels in the supercritical fluid have reached lower levels. This feature greatly extends the time between periodic cleaning of the quartz crystal microbalance.

As another feature of the present invention, an alternate system is provided for reducing unnecessary fouling of the quartz crystal microbalance. In accordance with this feature of the present invention, the sample stream is continually removed from the supercritical fluid and introduced into the measurement zone through a shutter system. The shutter system is closed when contaminant levels in the supercritical fluid are high. In the closed position, the shutter effectively prevents contaminants in the sample stream from contacting the quartz crystal microbalance. As the cleaning/extraction process progresses, the amount of contaminants will reach a sufficiently low level, at which time the shutter system is opened. In the open position, the contaminants are allowed to freely pass through the shutter for contact and measurement by the quartz crystal microbalance. The use of a shutter system also reduces the need for periodic cleaning of the quartz crystal microbalance system while eliminating the need for a high pressure valve to control flow of the sample stream.

The quartz crystal microbalance system includes a quartz crystal microbalance detector which is located within the measurement zone and includes a quartz crystal wafer. The quartz crystal wafer is exposed to the contaminants which deposit thereon. As a feature of the present invention, the quartz crystal wafer is periodically cleaned by exposing it to a solvent such as heptane at ambient pressure within the measurement zone. As an alternate feature of the present invention, the quartz crystal wafer may be subjected to cleaning utilizing supercritical fluid either in the measurement zone or by removing the quartz crystal microbalance detector and placing it in the cleaning chamber.

The above discussed and many other features and attendant advantages of the present invention will become better understood by reference to the following detailed description when taken in conjunction with the accompanying drawings.

DESCRIPTION OF THE PREFERRED EMBODIMENTS

The monitoring system in accordance with the present invention may be used to monitor contaminants present in a wide variety of supercritical fluids. The present invention is useful in monitoring both cleaning processes and extraction processes. The term "contaminants" is intended to cover both desirable and undesirable materials present in the supercritical fluid. For example, there may be instances in extraction processes when the material extracted into the supercritical fluid may be a desirable product which is isolated and recovered at a later time. For the purposes of this specification, such desirable materials present in the supercritical fluid will be classified and considered together with undesirable materials which are removed during a cleaning process and disposed of.

The following description will be limited to an exemplary system utilizing carbon dioxide as the critical fluid. It will be understood by those skilled in the art that the teachings set forth herein are applicable to any supercritical fluid system wherein the contaminants remain in a non-gaseous form when the supercritical fluid is converted to a gas at reduced pressures. The following description also will be limited to cleaning items to remove organic contaminants which are soluble in supercritical carbon dioxide fluid. However, it will also be understood that this system may be used for a variety of cleaning and/or extraction processes.

Figure 1:
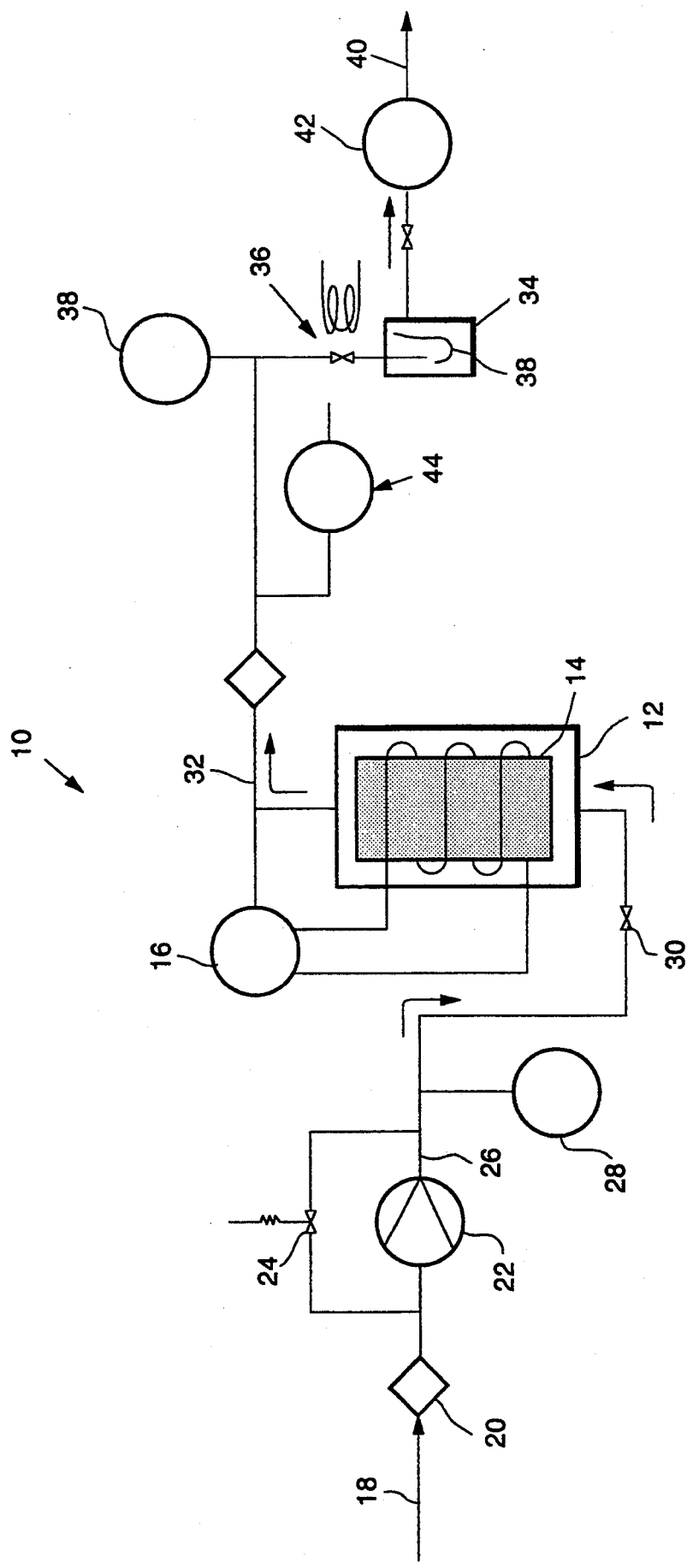
FIG. 1 is a schematic representation of a supercritical fluid cleaning/extraction system which includes a contaminant monitor in accordance with the present invention.

A preferred exemplary carbon dioxide supercritical fluid cleaning system is shown generally at 10 in FIG. 1. The system 10 includes a cleaning vessel 12 in which a piece of complex hardware 14 or other specimen is located for cleaning. The temperature within cleaning vessel 12 is maintained at a desired level by temperature controller 16 which controls heating elements (not shown) surrounding vessel 12. The temperature within cleaning vessel 12 is preferably maintained within a range of about 40° C. to 60° C. Carbon dioxide is introduced through line 18 into a high pressure filter 20. The carbon dioxide is then further compressed by an air-driven diaphragm compressor 22.

A pressure regulator 24 is provided for regulating the pressure in high pressure line 26 within a pressure range of between about 1200 psi to 5000 psi (or about 84 to 351 kg/cm$^2$). A pressure indicator 28 is provided to monitor the pressure level to insure that it remains within the desired range. The carbon dioxide in high pressure line 26 is in a supercritical fluid form. The supercritical fluid carbon dioxide is controllably introduced into vessel 12 by way of high pressure valve 30.

In cleaning vessel 12, the supercritical carbon dioxide fluid flows over the specimen 14 and extracts soluble materials, such as organic oils. The contaminated supercritical fluid is removed from the cleaning chamber 12 through line 32. The contaminated supercritical fluid is then passed into a separation/precipitation vessel 34. Prior to entry into the precipitation vessel 34, the supercritical fluid is converted into a gas in a heated expansion valve shown generally at 36. A pressure indicator 38 is provided for monitoring the pressure in line 32 just prior to reduction in pressure via heated expansion valve 36.

The contaminants which separate out from the gaseous carbon dioxide in separation vessel 34 are retained in a contaminant holder 38 and removed from the system. The clean carbon dioxide gas is then passed through line 40 for recycling back to line 18 for reuse in the system. A flow gauge 42 is provided for monitoring the amount of carbon dioxide gas being recycled to the system. Although it is preferred that the carbon dioxide gas be recycled for reuse in the cleaning system, it is not required.

Figure 2:
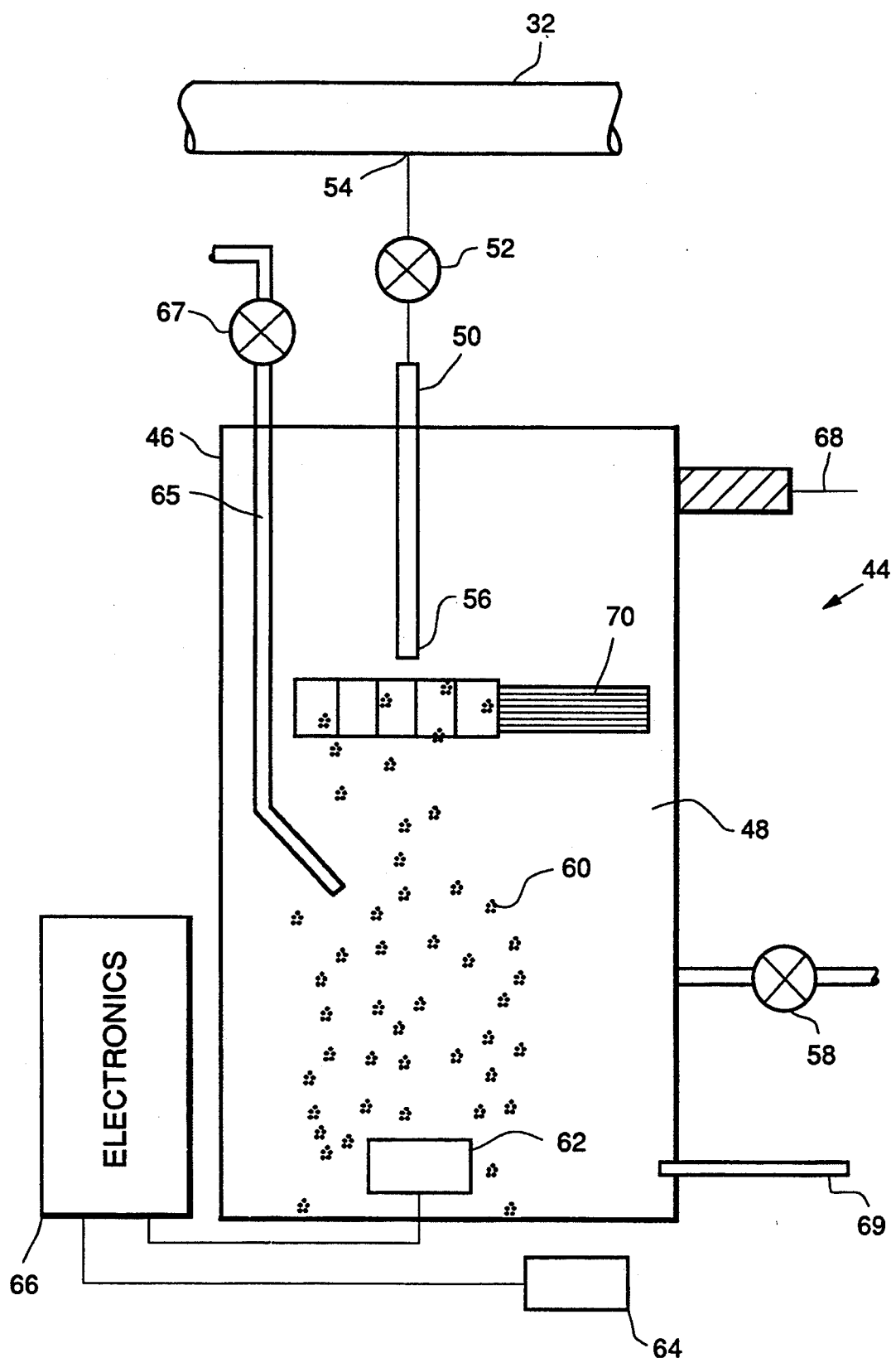
FIG. 2 is a partially diagrammatic representation of a preferred exemplary contaminant monitor in accordance with the present invention.

The system for monitoring changes in the amount of contaminants present in the flowing stream in accordance with the present invention is shown schematically at 44. Referring to FIG. 2, a more detailed partially schematic representation of the monitor 44 is shown. The monitor 44 includes a measurement vessel 46 which defines a measurement zone 48. Sampling means such as capillary tube 50 and valve 52 are provided for removing at least a portion of supercritical fluid from the stream flowing in line 32. The capillary tubing 50 has an inlet end 54 connected to line 32 and an outlet 56 located within the contaminant measurement zone 48. The valve 52 is a high pressure valve (with low dead space) which is operable between open and closed positions for controllably introducing the sample stream of supercritical carbon dioxide into the measurement zone 48. The capillary tube 50 is preferably made from glass which may or may not be metal coated. The outside diameter of the capillary tube is preferably on the order of 150 micrometers with the interior diameter of the capillary tubing being on the order of 15 to 50 micrometers. This configuration provides a flow rate of 10–200 ml/min. of gas at standard temperature and pressure Pressure release means, such as pressure relief valve 58, is provided to maintain the pressure within the measurement zone 48 at or below the level required to convert the sample stream exiting capillary tube 50 into a gas. Preferably, valve 58 will remain open so that the pressure within the measurement zone 48 is at atmospheric pressure. However, the relief valve 58 may be set to higher pressure levels on the order of a few hundred psi (or about 14 to 21 $Kg/cm^2$) provided that the pressure remains below the level at which the supercritical fluid exiting the capillary tube at outlet 56 is converted to gas.

In the reduced pressure environment of measurement vessel 48, the contaminants present in the sample stream remain in a non-gaseous, i.e. liquid or solid form. Some of the contaminant droplets, as represented at 60, adhere to a quartz crystal microbalance detector 62. Quartz crystal microbalances are commonly used in conventional electronic devices. The quartz crystal microbalance detector 62 includes a quartz crystal wafer which is exposed to the contaminants which deposit thereon. As the contaminants deposit on the quartz crystal wafer, the frequency at which the wafer is vibrating changes. This frequency is electronically mixed with the frequency of a quartz crystal microbalance reference 64. This establishes a beat frequency which is monitored through a frequency counter. The rate at which the frequency shifts is proportional to the amount of contaminants being deposited on the quartz crystal wafer, which in turn is an indicator of the cleanliness of the fluid in stream 32. As the amount of contaminants in the sample stream approaches zero, the rate of change of the quartz microbalance signal also drops to zero. Accordingly, use of the quartz crystal microbalance provides an accurate and sensitive way to detect when cleaning has been completed.

The quartz crystal microbalance detector 62, quartz crystal microbalance reference 64 and the electronics package 66 associated therewith will not be described in further detail since these items are of conventional design. A description of quartz crystal microbalances including their use and operation is set forth in the publication by A. W. Warner, "Micro Weighing with the Quartz Crystal Oscillator—Theory and Design," pages 137–161, in "Ultra MicroWeight Determination in Controlled Environments," S. P. Wolsky and E. J. Zdanuk, editors, Interscience Publishers, 1969, the contents of which are hereby incorporated by reference.

A cleaning drain 69 is located at the bottom portion of the measurement vessel to remove excess contaminants as they fall to the vessel bottom. Over a period of time, the contaminants which continually deposit on the quartz crystal microbalance detector 62 eventually render the microbalance inoperative. The quartz crystal microbalance detector 62 must then be cleaned to remove the contaminant deposits. After cleaning, the quartz crystal microbalance detector may be reused.

Cleaning of the quartz crystal microbalance detector 62 may be accomplished in a number of different ways. Preferably, the detector 62 is cleaned by backwashing the measurement vessel 46 with supercritical fluid. For example, pressure relief valve 58 is closed, and supercritical fluid is then introduced into the measurement zone 48 by way of line 68. Sufficient supercritical fluid is introduced through line 68 into the measurement zone 48 to insure complete washing of contaminants from detector 62. The resulting contaminated supercritical fluid can then be vented through valve 58 and/or cleaning drain 69.

In an alternative cleaning process, the detector 62 is removed from the measurement zone 48 and cleaned using conventional organic solvents. If desired, multiple quartz crystal microbalance detectors may be loaded on a carousel within measurement vessel 46 with a fresh detector being rotated into position under capillary tube 50 as the previous detector becomes overloaded. When all of the detectors in a carousel become overloaded, a clean carousel is inserted into the measurement zone 48. The carousel of spent detectors is then subjected to cleaning with conventional solvents or supercritical fluids.

Cleaning of microbalance detector 62 can also be accomplished within vessel 46 by introducing cleaning solvent through line 65. Valve 67 is provided to control the solvent when it is introduced into contact with the detector 62. This in situ cleaning using solvent is preferably carried out at ambient pressure. The resulting contaminated wash solvent is removed through line 69.

During the initial stages of the cleaning process, the amount of contaminants present in line 32 is much higher than at later stages. Monitoring of the supercritical fluid stream early in the cleaning process is not desirable and generally not necessary. Due to the increased amounts of contaminants present in the supercritical fluid at the early cleaning stages, the detector 62 becomes fouled much more quickly. Accordingly, it is preferred to provide some means for preventing contaminants in the sample stream from contacting the detector 62 during early stages of the cleaning process. For example, valve 52 is preferably closed during the early stages of cleaning and only opened after sufficient processing time has elapsed to substantially reduce contaminant levels in line 32.

Alternatively, valve 52 may be left open or deleted entirely from the system to provide continuous removal of a sample stream from line 32. A shutter 70 is then provided which is operable between an open position wherein contaminants pass freely by the shutter and a closed position where the contaminants are retained by the shutter. The shutter 70 is shown in the open position in FIG. 2 wherein contaminant particles are allowed to fall directly onto the detector 62. The use of valve 52 and/or shutter 70 is particularly preferred when cleaning especially dirty parts or when monitoring extraction processes. The valve 52 and shutter 70 are not required when the system 44 is used to monitor cleaning of trace contaminants from relatively clean electronic assemblies and complex hardware.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A system for monitoring contaminants present in a flowing stream of supercritical fluid wherein the amount of said contaminants decreases with time, said system comprising:
   a tube for containing said flowing stream of supercritical fluid;
   a contaminant measurement zone connected to said tube;
   sampling means for removing at least a portion of supercritical fluid from said flowing stream and introducing said portion of supercritical fluid into said contaminant measurement zone as a sample stream;
   pressure release means connected to said measurement zone for maintaining the pressure within said measurement zone at or below the level required to convert said sample stream into a gas wherein said contaminants present in said sample stream remain in a non-gaseous form in said measurement zone;
   a quartz crystal microbalance system in said measurement zone, on which said contaminants deposit in non-gaseous form for measuring changes in the amount of contaminants introduced into said measurement zone by said sample stream to thereby provide for monitoring of decreases in the amount of contaminants in said flowing stream of supercritical fluid.

2. A system for monitoring contaminants present in a flowing stream of supercritical fluid according to claim 1 wherein said sampling means comprises a capillary sampling tube having an inlet connected to said tube containing said flowing stream of supercritical fluid and an outlet located within said contaminant measurement zone through which said sample stream is introduced into said measurement zone.

3. A system for monitoring contaminants present in a flowing stream of supercritical fluid according to claim 2 wherein said sampling means includes a sampling valve operable between open and closed positions for controllably introducing said sample stream into said measurement zone.

4. A system for monitoring contaminants present in a flowing stream of supercritical fluid according to claim 2 wherein said sampling means includes means located in said measuring zone adjacent to said outlet of said capillary tube for controllably removing contaminants from said sample stream as said sample streams exits said capillary tube through said outlet.

5. A system for monitoring contaminants present in a flowing stream of supercritical fluid according to claim 4 wherein said means for controllably removing contaminants from said sample stream comprises a shutter located adjacent to said capillary tube outlet, said shutter being operable between an open position wherein contaminants are not captured by said shutter and a closed position wherein said contaminants are captured by said shutter and removed from said sample stream.

6. A system for monitoring contaminants present in a flowing stream of supercritical fluid according to claim 1 wherein said measurement zone is located within a measurement vessel and wherein said pressure release means comprises a pressure relief opening in said vessel to allow escape of gas from said vessel to maintain the pressure in said measurement zone at an ambient level.

7. A system for monitoring contaminants present in a flowing stream of supercritical fluid according to claim 1 wherein said quartz crystal microbalance system comprises a quartz crystal microbalance detector located within said measurement zone wherein said detector comprises a quartz crystal wafer which is exposed to said contaminants which deposit thereon, said system further including means for periodically cleaning said contaminants from said quartz crystal wafer.

8. A system for monitoring contaminants present in a flowing stream of supercritical fluid according to claim 7 wherein said pressure release means further comprises a pressure valve connected to said pressure relief opening, said pressure valve being operable between a closed position to provide pressurization of said vessel and an open position.

9. A system for monitoring contaminants present in a flowing stream of supercritical fluid according to claim 7 wherein said means for periodically cleaning deposited contaminants from said quartz crystal wafer comprises:
   a cleaning fluid inlet in said vessel;
   means for introducing cleaning fluid into contact with said quartz crystal wafer to produce used cleaning fluid containing contaminants removed from said quartz crystal wafer; and
   means for removing said used cleaning fluid from said vessel.

10. A system for monitoring contaminants present in a flowing stream of supercritical fluid according to claim 7 wherein said quartz crystal microbalance system comprises a quartz crystal microbalance reference and means for establishing a beat frequency between said quartz crystal microbalance detector and said quartz crystal microbalance reference wherein changes in said beat frequency provide an indication of changes in the amount of contaminants introduced into said measurement zone.

11. A method for monitoring contaminants present in a flowing stream of supercritical fluid comprising the steps of:
   removing at least a portion of supercritical fluid from said flowing stream and introducing said portion of supercritical fluid into a contaminant measurement zone as a sample stream;
   maintaining the pressure within said measurement zone at or below the level required to convert said sample stream into a gas wherein said contaminants present in said sample stream remain in a non-gaseous form;
   using a quartz crystal microbalance system in said measurement zone to measure changes in the amount of contaminants introduced into said measurement zone by said sample stream wherein contaminants deposit on said quartz crystal microbalance system to thereby provide for monitoring of changes in the amount of contaminants in said flowing stream of supercritical fluid.

12. A method for monitoring contaminants present in a flowing stream of supercritical fluid according to claim 11 wherein said sample stream is introduced into said measurement zone through a capillary sampling tube.

13. A method for monitoring contaminants present in a flowing stream of supercritical fluid according to claim 12 wherein said sample stream is removed from said flowing stream and introduced into said measurement zone only after a preselected amount of time has elapsed.

14. A method for monitoring contaminants present in a flowing stream of supercritical fluid according to claim 13 wherein contaminants present in said sample stream are removed to prevent measurement by said quartz crystal microbalance system until a preselected amount of time has elapsed.

15. A method for monitoring contaminants present in a flowing stream of supercritical fluid according to claim 14 wherein said contaminants are selectively removed from said sample stream by a shutter which is operable between an open position wherein contaminants are not captured by said shutter and a close position wherein said contaminants are captured by said shutter and removed from said sample stream.

16. A method for monitoring contaminants present in a flowing stream of supercritical fluid according to claim 11 wherein said pressure in said measurement zone is maintained at approximately ambient pressure.

17. A method for monitoring contaminants present in a flowing stream of supercritical fluid according to claim 11 wherein said quartz crystal microbalance system comprises a quartz crystal microbalance detector located within said measurement zone wherein said detector comprises a quartz crystal detector wafer which is exposed to said contaminants which deposit thereon, said method further including the step of periodically cleaning said contaminants from said quartz crystal detector wafer.

18. A method for monitoring contaminants present in a flowing stream of supercritical fluid according to claim 17 wherein said step of periodically cleaning said quartz crystal detector wafer is accomplished by cleaning said wafer with supercritical fluid.

19. A method for monitoring contaminants present in a flowing stream of supercritical fluid according to claim 17 wherein said step of periodically cleaning said quartz crystal detector wafer is accomplished by cleaning said wafer at ambient pressure with a cleaning fluid.

20. A method for monitoring contaminants present in a flowing stream of supercritical fluid according to claim 17 wherein said method includes the step of providing a quartz crystal microbalance reference which comprises a quartz crystal reference wafer and establishing a beat frequency between said quartz crystal detector wafer and said quartz crystal reference wafer, wherein changes in said beat frequency provide an indication of changes in the amount of contaminants introduced into said measurement zone.

* * * * *